United States Patent [19]

Drent et al.

[11] Patent Number: 5,488,175
[45] Date of Patent: Jan. 30, 1996

[54] HYDROFORMYLATION PROCESS

[75] Inventors: Eit Drent; Willem W. Jager, both of Amsterdam, Netherlands

[73] Assignee: Shell Oil Company, Houston, Tex.

[21] Appl. No.: 304,716

[22] Filed: Sep. 12, 1994

[30] Foreign Application Priority Data

Sep. 16, 1993 [EP] European Pat. Off. ............ 93202688

[51] Int. Cl.⁶ .................................... C07C 45/50
[52] U.S. Cl. ................ 568/454.000; 568/426.000; 568/429.000; 568/456.000; 568/455.006
[58] Field of Search .................... 568/426, 454, 568/455, 429, 451

[56] References Cited

U.S. PATENT DOCUMENTS

| | | | |
|---|---|---|---|
| 3,946,082 | 3/1976 | McVicker | 260/604 |
| 4,358,621 | 11/1982 | Sakakibara et al. | 568/454 |
| 4,668,809 | 5/1987 | Oswald et al. | 556/18 |
| 4,687,874 | 8/1987 | Oswald et al. | |
| 4,774,362 | 9/1988 | Devon et al. | 568/454 |

FOREIGN PATENT DOCUMENTS

| | | |
|---|---|---|
| 158518 | 10/1985 | European Pat. Off. . |
| 0279018A1 | 8/1988 | European Pat. Off. . |
| 0293818A2 | 12/1988 | European Pat. Off. . |
| 0375573A1 | 6/1990 | European Pat. Off. . |
| 0491239A2 | 6/1992 | European Pat. Off. . |
| 1424818 | 2/1976 | United Kingdom . |
| 2014138 | 8/1979 | United Kingdom . |

OTHER PUBLICATIONS

J. Falbe, "New Syntheses with Carbon Monoxide", Springer Verlag, Berlin 1980, pp. 107 and 108.

*J. Mol. Catal.* (1987) 41 (1–2) 163–183 and Chemical Abstracts 109:6609 (Halcon).

*Chim. Ind.* (Milan) (1978) 60 (11) 887–891 and Chemical Abstract 90:93043 (Montedison).

Primary Examiner—Werren B. Lone

[57] ABSTRACT

A process for the hydroformylation of unsaturated compounds containing a group C=C=C—OH, in the presence of a catalyst system containing rhodium and a ligand of the formula $R^1R^2P$—R—$NR^3R^4$ wherein $R^1$, $R^2$, $R^3$ and $R^4$ independently represent a substituted or unsubstituted hydrocarbyl group and R represents a bivalent organic bridging group containing from 1 to 5 atoms in the bridge.

21 Claims, No Drawings

1

HYDROFORMYLATION PROCESS

FIELD OF THE INVENTION

The invention relates to a process for the hydroformylation of unsaturated compounds by reaction thereof with carbon monoxide and hydrogen in the presence of a rhodium containing catalyst.

BACKGROUND OF THE INVENTION

The hydroformylation of unsaturated compounds is a well-established process which for many years has been operated on a commercial scale.

In most cases, olefins are used as starting material, but it is known that the hydroformylation of other ethylenically unsaturated compounds such as unsaturated esters and unsaturated alcohols can be successfully performed as well.

However, the presence of substituents in ethylenically unsaturated compounds may cause problems, even if the substituents as such do not interfere with the hydroformylation reaction proper. For example, in the hydroformylation of certain unsaturated alcohols, especially allyl alcohols, isomerization of the starting material occurs as a side-reaction (cf J.Falbe "New Syntheses with Carbon Monoxide", 1980 pp 107 and 108) to form aldehydes, at the expense of the yield of the desired hydroformylation product, viz. hydroxy aldehydes. While the said isomerization is a typical side reaction in hydroformylation processes whereby a cobalt-containing catalyst is used, it also occurs, albeit to a lesser extent, when rhodium-containing hydroformylation catalysts are applied. In fact, rhodium catalyzed processes are known, whereby with the aid of special measures the said isomerization even becomes the predominant reaction (cf EP 293.818).

A process for the hydroformylation of lower olefins (or substituted olefins such as allyl alcohol), whereby it is envisaged to optimize the hydroformylation conditions and to minimize the formation of undesirable by-products, is described in GB 2014138. In this process use is made of a catalyst system, comprising a rhodium complex, a tri-substituted phosphine and a diphosphino alkane wherein 2, 3 or 4 aryl groups are present, linked to the two phosphorus atoms.

According to the examples relating to the hydroformylation of allyl alcohol, a rate of about 1650 (moles of product per gram atom of rhodium and per hour) is achieved, while 6.5% of propionaldehyde (isomerization product) is formed.

Another process for the hydroformylation of unsaturated compounds, including that of allyl alcohol, is disclosed in EP 279018. According to this document, the reaction is carried out in the presence of a catalyst system, comprising rhodium in a chemical complex with one or more ligands of the formula $$\begin{array}{c} R_1 \quad R^3 \\ \diagdown \quad \diagdown \\ Y-C_x-Ar_y-Ar_x-C-Y \\ \diagup \quad \diagup \\ R_2 \quad R_4 \end{array} \begin{array}{c} R_3 \quad R_1 \\ | \quad \diagup \\ \\ | \quad \diagdown \\ R_4 \quad R_2 \end{array},$$

and the y bond are linked to adjacent carbon atoms of the ring structure Ar, the groups Ar may contain up to 4 substituents, $R_1$ to $R_4$ are specific hydrocarbyl groups, $R_3$ and $R_4$ may additionally be hydrogen and the groups Y are independently selected from the elements N, P, As, Sb and Bi.

According to one of the examples allyl alcohol is converted at a rate of about 2700 (moles of product per gram atom of rhodium and per hour), whereby in addition to the desired hydroformylation products 4.4% of propionaldehyde is formed.

In U.S. Pat. No. 4,668,809, a hydroformylation process is disclosed in which as catalyst a rhodium-containing complex is used, additionally comprising a diarylphosphinoalkyl substituted hetero-organic ligand. The document discloses a large number of compounds that may be used as catalyst ligand and indicates a variety of unsaturated compounds, such as substituted and non-substituted olefinic substances that may be applied as starting material.

However, no working example is included, relating to the hydroformylation of allyl alcohol.

It has now been found that, in the hydroformylation of unsaturated alcohols, the rate is increased and the formation of isomerized by-products is further reduced, by selecting a catalyst system which is based on rhodium in combination with certain ligands, containing both phosphorus and nitrogen.

SUMMARY OF THE INVENTION

The invention therefore relates to a process for the hydroformylation of unsaturated compounds in which a compound containing a group $$\begin{array}{c} \diagdown \quad \quad H \\ \quad \quad | \quad | \\ C=C-C-OH \\ \diagup \quad \quad | \end{array}$$

is reacted with carbon monoxide and hydrogen in the presence of a catalyst system based on
 a) a source of rhodium and
 b) a ligand of the formula $$R^1R^2P-R-NR^3R^4 \quad \quad (I)$$

wherein each of $R^1$, $R^2$, $R^3$ and $R^4$ independently represents a substituted or non-substituted hydrocarbyl group and R represents a bivalent organic bridging group containing from 1 to 5 atoms in the bridge.

DESCRIPTION OF THE PREFERRED EMBODIMENTS

According to an accepted reaction scheme, the hydroformylation of compounds containing a group $$\begin{array}{c} \diagdown \quad \quad | \\ C=C-C-OH \\ \diagup \quad | \quad | \\ \quad \quad H \end{array}$$

will result in the formation of compounds containing a group $$\begin{array}{c} \quad \quad H \quad H \\ \quad \quad | \quad | \quad | \\ O=C-C-C-C-OH \\ \quad \quad | \quad | \quad | \quad | \\ \quad \quad H \end{array}$$

and compounds containing a group

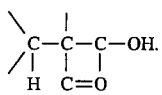

To the free valencies indicated in the groups occurring in the starting material and the hydroformylation products, preferably hydrogen atoms are attached. Alternatively, alkyl groups may be attached to one or more of these free valencies, in particular alkyl groups having from 1 to 3 carbon atoms, methyl groups being preferred. Thus, suitable starting materials include 3-butene-2-ol, methallyl alcohol and allyl alcohol. Preferably, allyl alcohol is used as starting material.

The resulting hydroformylation products are suitable as intermediates for the preparation of valuable chemicals, such as 1,3-diols and 1,4-diols, for example, 1,3-methylpropanediol and 1,4-butanediol.

If the starting material contains a group

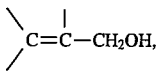

isomerization would produce an aldehydes, containing a group

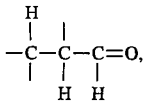

whereas isomerization of a compound containing a group

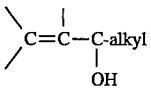

would result in the formation of a ketone, containing a group

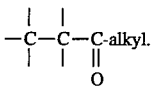

With the catalyst systems of the invention, the formation of these by-products, resulting from isomerization of the starting material, is significantly reduced, e.g. to amounts of say 2% or less, based on the starting material. The catalyst systems of the invention, as regards component a), are based on a source of rhodium. Suitable sources of rhodium include rhodium compounds, in particular rhodium salts, such as rhodium nitrate and rhodium chloride and rhodium complexes, such as dirhodium octacarbonyl, tetrarhodium dodecacarbonyl and hexarhodium hexadecacarbonyl.

Preferred sources of rhodium are organic rhodium compounds, such as rhodium carboxylates and organic rhodium carbonyl compounds. Examples of suitable organic rhodium compounds are rhodium acetate, rhodium di(carbonyl) acetylacetonate, rhodium trioctanoate, 1,5-cyclooctadiener- hodium (I) acetate and 1,5-cyclooctadiene-rhodium (I) acetylacetonate. Rhodium di(carbonyl) acetylacetonate is in particular preferred.

In view of the high price of rhodium, it is recommended to limit the amount of rhodium present in the catalyst as much as technically feasible. Generally, the required amount of rhodium is in the range of $10^{-7}$ to $5.10^{-1}$ gram atom of rhodium per mol of unsaturated compound to be hydroformylated. Preferably the amount of rhodium is selected in the range of $10^{-6}$ to $10^{-1}$, on the same basis.

The ligands of formula (I), component b) of the catalyst system according to the invention, comprise a trivalent phosphorus atom which is linked via a bivalent organic bridging group to a nitrogen atom. Without wishing to speculate on the specific structure of the actual catalyst complex during the reaction, it is considered likely that at some stage rhodium is coordinated with phosphorus as well as nitrogen. It is believed that the structure of the remaining groups linked to the phosphorus and the nitrogen atom, i.e. the groups represented by $R^1$, $R^2$, $R^3$ and $R^4$, as well as the structure of the bridging group R, are of relevance for achieving an optimal coordination between rhodium and the ligand. The groups $R^1$ and $R^2$ which are linked to the phosphorus atom in the ligands of formula (I), are preferably substituted or non- substituted aryl groups. They may be similar or dissimilar, similar groups being preferred. In particular preferred are ligands in which $R^1$ and $R^2$ each represent a phenyl group.

As regards the groups represented by R3 and $R^4$, substituted or non-substituted alkyl groups are considered especially suitable. Preferably, each of $R^3$ and $R^4$ represents a substituted or unsubstituted alkyl group having from 1 to 4 carbon atoms. Most preferred are ligands wherein $R^3$ and $R^4$ each represent a methyl group.

Any substituents present in one or more of the groups represented by $R^1$, $R^2$, $R^3$, and $R^4$, are advantageously selected from halogen atoms, such as chlorine and fluorine atoms, cyano groups and alkoxy groups such as ethoxy- and methoxy groups.

The bivalent group R in the ligands of formula (I), interlinking the phosphorus and the nitrogen atom, is preferably an organic bridging group containing from 1 to 4 carbon atoms in the bridge. The bridging group may be an alkylene chain, substituted or unsubstituted, and possibly interrupted by one or two hetero atoms, in particular oxygen atoms. However, preferably R represents an unsubstituted alkylene group with one to three carbon atoms, in particular an ethylene group.

The amount of ligand of formula (I), supplied to form the catalyst system is not critical, but is usually in excess of the amount of rhodium, expressed in moles of ligand per gram atom of rhodium. Preferred amounts are in the range of 2 to 20 moles of ligand per gram atom of rhodium.

The hydroformylation process of the invention is preferably carried out in a non-acidic medium. If desired, the (non)acidity of the medium can be controlled by adding alkaline compounds such as amides or, preferably, tertiary amines.

The presence of a separate solvent is not strictly necessary, since the starting material may often serve as the liquid reaction medium. However, the use of an inert solvent is sometimes preferred, for economic reasons, or when an unusual starting material is used, of which large quantities may not be readily available. Suitable solvents include alcohols, such as methanol, butanol, hexanol and 2-ethylhexanol, esters such as methyl acetate, ethylacetate, methyl propionate and butylpropionate, ethers such as anisole, 2,5,8 trioxanonane (diglyme) and tetrahydrofuran and ketones such as acetone and methylethylketone.

Preferably, as solvent an ester is applied.

The hydroformylation reaction of the invention is carried out at moderate reaction conditions. In general, temperatures are selected in the range of about 20° C. to about 200° C., preferably in the range of about 50° C. to about 120° C.

Suitable pressures can vary widely, but it is recommended to apply a pressure in the range of about 5 bar to about 100 bar. The gaseous hydroformylation reactants, i.e., hydrogen and carbon monoxide may be supplied, diluted with inert gases such as nitrogen, but are usually supplied as such. The said gaseous reactants are preferably provided in such amounts that the molar ratio is in the range of about 4:1 to about 1:4. Substantially equimolar amounts are most preferred.

The invention is further illustrated by the following non-limiting examples which are not to be construed as limiting the scope of the present specification and claims.

ILLUSTRATIVE EMBODIMENTS

All experiments were carried out in a 250 mL, magnetically stirred, "Hastelloy" (trade mark) autoclave.

EXAMPLE I

The reactor was charged with 10 milliliters (mL) of allylalcohol, 0.1 mmol of rhodium di(carbonyl) acetylacetonate, 1 mmol of 1-diphenylphosphino, 2-dimethylaminoethane and 40 mL of butylpropionate.

The autoclave was flushed with an equimolar mixture of carbon monoxide and hydrogen and pressurized up to a total pressure of 60 bar, the partial pressures of CO and $H_2$ each being 30 bar. The autoclave was sealed and the mixture was heated to the reaction temperature of 95° C.

Upon completion of the reaction, the contents of the autoclave were cooled to room temperature and the pressure was released.

The catalyst components, solvent, reaction temperature, the reaction rate (expressed in moles of product per gram atom of rhodium and per hour) and the selectivity and linearity of the product obtained, are shown in Table 1. The hydroformylation products are mainly the linear 4-hydroxybutyraldehyde and the non-linear 2-methyl 3-hydroxypropionaldehyde.

EXAMPLES II–VIII

In substantially the same manner as described in Example I, a number of experiments were carried out, whereby allyl alcohol was hydroformylated with the aid of a catalyst system according to the invention.

The catalyst components, solvent, reaction temperature, the reaction rate and the selectivity and linearity of the product are shown in Table 1.

Comparative Example A

In a similar manner as described in the previous Examples, an experiment was carried out, whereby however, 0.5 mol of triphenylphosphine was used as catalyst ligand, instead of a ligand containing both phosphorus and nitrogen.

The conditions and results are included in Table 1, showing that with triphenylphosphine as catalyst ligand the hydroformylation proceeds at a lower rate than with a catalyst ligand according to the invention. Moreover, in the comparative experiment isomerization took place, resulting in the formation of a significant amount of propionaldehyde.

TABLE I

| Ex. No. | Catalyst | | | | Solvent mL | | Temp. °C. | Rate mol/gat. hr | Selectivity to hydroform. products, % | Linearity % |
|---|---|---|---|---|---|---|---|---|---|---|
| | Rh. comp. mmol | | Ligand mmol | | | | | | | |
| I | RDCA, | 0.1 | DPDE, | 1 | butylpropionate, | | 40 | 95 | 12,000 | >98 | 67 |
| II | RDCA, | 0.1 | DPDE, | 0.5 | butylpropionate, triethylamine, | 10 | 40 | 95 | 10,000 | >98 | 69 |
| III | RDCA, | 0.1 | DPDE, TPP, | 0.24 1 | butylpropionate, | | 40 | 85 | 12,000 | >98 | 72 |
| IV | RDCA, | 0.1 | DPDE, | 0.5 | hexanol, | | 40 | 90 | 8,000 | >98 | 63 |
| A | RDCA, | 0.1 | TPP, | 0.5 | hexanol, | | 40 | 90 | 2,000 | >98 (6% propionaldehyde) | 65 |
| V | RDCA, | 0.1 | DPDM, | 0.5 | butylpropionate, | | 40 | 85 | 10,000 | 97 (1% propionaldehyde) | 67 |
| VI | RDCA, | 0.1 | DPDM, | 0.5 | butylpropionate, | | 50 | 80 | 6,000 | 96 (2% propionaldehyde) | 72 |
| VII | RDCA, | 0.1 | DPDE, | 0.5 | methanol, | | 50 | 80 | 6,000 | 98 | 60 |
| VIII | RTO, | 0.1 | DPDE, | 0.5 | hexanol, | | 40 | 85 | 8,000 | >98 | 69 |

The abbreviations used in the Table have the following meaning:
RDCA = Rhodium di(carbonyl)acetylacetonate
RTO = Rhodium trioctanoate
DPDE = 1-Diephenylphosphino, 2-dimethylamino ethane
DPDM = Diephenylphosphino (dimethylamino)methane
TPP = Triphenylphosphine

What is claimed is:

1. A process for the hydroformylation of unsaturated compounds to produce compounds containing a group $$O=C-\underset{H}{\overset{H}{\underset{|}{C}}}-\overset{H}{\underset{|}{C}}-\overset{H}{\underset{|}{C}}-OH$$

and compounds containing a group $$\underset{H}{\overset{\diagdown}{\diagup}}C-\underset{C=O}{\overset{|}{C}}-\overset{|}{C}-OH$$

which comprises contacting and reacting a compound containing a group

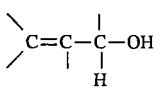

with carbon monoxide and hydrogen in the presence of a catalyst system comprising:

a) a source of rhodium and
b) a ligand of the formula

wherein each of $R^1$, $R^2$, $R^3$, and $R^4$ independently represents a substituted or unsubstituted hydrocarbyl group and R represents a bivalent organic bridging group containing from 1 to 5 atoms in the bridge.

2. The process as claimed in claim 1, wherein the unsaturated compound used as starting material contains a group

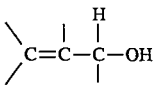

in its molecule whereby each of the free valencies is linked to a hydrogen atom or a substituted or unsubstituted alkyl group having from 1 to 3 carbon atoms.

3. The process as claimed in claim 2, wherein the unsaturated compound contains a group

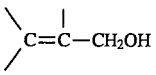

in its molecule.

4. The process as claimed in claim 3, wherein the unsaturated compound is allylalcohol.

5. The process as claimed in claim 1, wherein said source of rhodium is an organic rhodium compound.

6. The process as claimed in claim 5, said organic rhodium compound is rhodium di(carbonyl)acetylacetonate.

7. The process as claimed in claim 1 wherein in said ligand of formula (I), each of $R^1$ and $R^2$ independently represent a substituted or unsubstituted aryl group.

8. The process as claimed in claim 7, wherein $R^1$ and $R^2$ each represent a phenyl group.

9. The process as claimed in claim 1, wherein in said ligand of formula (I), each of $R^3$ and $R^4$ independently represents a substituted or unsubstituted alkyl group having from 1 to 4 carbon atoms.

10. The process as claimed in claim 9, wherein $R^3$ and $R^4$ each represent a methyl group.

11. The process as claimed in claim 1, wherein in said ligand of formula (I), R represents a bivalent organic bridging group containing from 1 to 4 carbon atoms in the bridge.

12. The process as claimed in claim 11, wherein R represents an ethylene group.

13. The process as claimed in claim 1, wherein said catalyst system contains an amount of ligand of formula (I) in the range of 2 to 20 moles per gram atom of rhodium.

14. The process as claimed in claim 1, wherein said catalyst system contains an amount of rhodium in the range of $10^{-6}$ to $10^{-1}$ gram atom per mole of unsaturated compound.

15. The process as claimed in claim 1, wherein said process is carried out in a non-acidic medium.

16. The process as claimed in claim 1, wherein said process is carried out in the presence of a tertiary amine.

17. The process as claimed in claim 1, wherein said process is carried out in the presence of a solvent.

18. The process as claimed in claim 17, wherein said solvent is an ester.

19. The process as claimed claim 1, wherein said process is carried out at a temperature in the range of about 50° C. to about 120 ° C.

20. The process as claimed in claim 1, wherein said process is carried out at a pressure in the range of about 5 bar to about 100 bar.

21. The process as claimed in claim 1, wherein, in said process, the molar ratio of carbon monoxide to hydrogen is in the range of about 4:1 to about 1:4.

* * * * *